United States Patent
Farrell et al.

(10) Patent No.: US 10,213,157 B2
(45) Date of Patent: Feb. 26, 2019

(54) ACTIVE UNIPOLAR DRY ELECTRODE OPEN EAR WIRELESS HEADSET AND BRAIN COMPUTER INTERFACE

(71) Applicant: BOSE CORPORATION, Framingham, MA (US)

(72) Inventors: Andrew Farrell, Boston, MA (US); Christopher R. Paetsch, Cambridge, MA (US); Tegan M. Ayers, Waltham, MA (US); Jack E. Read, Marlborough, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 15/618,388

(22) Filed: Jun. 9, 2017

(65) Prior Publication Data
US 2018/0353128 A1 Dec. 13, 2018

(51) Int. Cl.
*G08C 19/22* (2006.01)
*H04Q 9/00* (2006.01)
(Continued)

(52) U.S. Cl.
CPC .......... *A61B 5/6803* (2013.01); *A61B 5/0006* (2013.01); *A61B 5/0478* (2013.01);
(Continued)

(58) Field of Classification Search
CPC . A61B 5/6803; A61B 5/0006; A61B 5/04085; A61B 5/0478; A61B 5/0482; A61B 5/0492; A61B 5/0496; A61B 5/1103; A61B 5/1123; A61B 5/165; A61B 5/4542; A61B 5/4803; A61B 5/7203; A61B 2560/0209; A61B 2562/0209; A61B 2562/06
See application file for complete search history.

(56) References Cited

U.S. PATENT DOCUMENTS

| 6,353,396 B1* | 3/2002 | Atlas | G08B 21/06 340/575 |
| 8,706,206 B2* | 4/2014 | Kanai | A61B 5/18 600/500 |

(Continued)

FOREIGN PATENT DOCUMENTS

| WO | 2005020841 A2 | 3/2005 |
| WO | 2014205327 A1 | 12/2014 |

(Continued)

OTHER PUBLICATIONS

Tronstad, et al. "Electrical Measurement of Sweat Activity", Physiological Measurement, vol. 29, No. 6, Jun. 1, 2008, pp. S409-S415.

(Continued)

*Primary Examiner* — Quang Pham
(74) *Attorney, Agent, or Firm* — Patterson + Sheridan, LLP

(57) ABSTRACT

Aspects of the present disclosure provide a wearable audio product for obtaining biologically-relevant information associated with a user comprising. The audio product comprises a first electrode placed over the user's auditory cortex on a first side of the user's body, a second electrode placed on the first side of the user's body, a first reference electrode placed on the first side of the user's body, a processor coupled to the first, second, and first reference electrode, the processor configured to take one or more actions based on signals received from the first, second, and first reference electrodes, and an electroacoustic transducer coupled to the processor. Any or all of the electrodes described herein may include any integer number of electrodes clustered in the specified location.

16 Claims, 6 Drawing Sheets

(51) Int. Cl.
*A61B 5/00* (2006.01)
*A61B 5/16* (2006.01)
*A61B 5/11* (2006.01)
*A61B 5/0408* (2006.01)
*A61B 5/0478* (2006.01)
*A61B 5/0482* (2006.01)
*A61B 5/0492* (2006.01)
*A61B 5/0496* (2006.01)

(52) U.S. Cl.
CPC ........ *A61B 5/0482* (2013.01); *A61B 5/04085* (2013.01); *A61B 5/0492* (2013.01); *A61B 5/0496* (2013.01); *A61B 5/1103* (2013.01); *A61B 5/1123* (2013.01); *A61B 5/165* (2013.01); *A61B 5/4542* (2013.01); *A61B 5/4803* (2013.01); *A61B 5/7203* (2013.01); *A61B 2560/0209* (2013.01); *A61B 2562/0209* (2013.01); *A61B 2562/06* (2013.01)

(56) References Cited

U.S. PATENT DOCUMENTS

| | | | |
|---|---|---|---|
| 9,474,876 B1* | 10/2016 | Kahn | A61M 21/02 |
| 9,516,442 B1* | 12/2016 | Dusan | H04R 29/001 |
| 2004/0073129 A1* | 4/2004 | Caldwell | A61B 5/0478 600/544 |
| 2004/0252103 A1* | 12/2004 | Bonnat | G06F 1/16 345/156 |
| 2005/0192514 A1 | 9/2005 | Kearby et al. | |
| 2007/0066914 A1* | 3/2007 | Le | A61B 5/0476 600/544 |
| 2007/0112277 A1* | 5/2007 | Fischer | A61B 5/0006 600/544 |
| 2008/0146892 A1* | 6/2008 | LeBoeuf | G16H 50/30 600/300 |
| 2008/0187147 A1* | 8/2008 | Berner | F24F 13/24 381/71.3 |
| 2008/0306398 A1* | 12/2008 | Uchiyama | A61B 5/0002 600/544 |
| 2010/0217100 A1 | 8/2010 | LeBoeuf et al. | |
| 2011/0040202 A1* | 2/2011 | Luo | A61B 5/04842 600/544 |
| 2011/0071416 A1* | 3/2011 | Terada | A61B 5/0478 600/544 |
| 2012/0128166 A1* | 5/2012 | Kim | H04R 3/005 381/58 |
| 2012/0165695 A1* | 6/2012 | Kidmose | A61B 5/0476 600/545 |
| 2012/0203079 A1* | 8/2012 | McLaughlin | A61B 5/04012 600/301 |
| 2012/0226127 A1* | 9/2012 | Asjes | A61B 5/04085 600/383 |
| 2012/0238856 A1* | 9/2012 | Kidmose | A61B 5/0482 600/379 |
| 2012/0289869 A1* | 11/2012 | Tyler | A61N 7/00 601/2 |
| 2013/0056010 A1* | 3/2013 | Walker | A61M 16/024 128/848 |
| 2013/0131537 A1* | 5/2013 | Tam | A61B 5/4854 600/544 |
| 2013/0234823 A1* | 9/2013 | Kahn | A61M 21/02 340/3.1 |
| 2013/0242262 A1* | 9/2013 | Lewis | G02B 27/0093 351/209 |
| 2013/0317382 A1* | 11/2013 | Le | A61B 5/04 600/544 |
| 2013/0338738 A1* | 12/2013 | Garcia Molina | G09B 19/00 607/90 |
| 2013/0343585 A1* | 12/2013 | Bennett | H04R 25/554 381/315 |
| 2014/0051940 A1 | 2/2014 | Messerschmidt | |
| 2014/0135644 A1* | 5/2014 | Kim | A61B 5/6803 600/545 |
| 2014/0136450 A1* | 5/2014 | Lee | G06N 7/005 706/11 |
| 2014/0148657 A1* | 5/2014 | Hendler | A61B 5/0476 600/301 |
| 2014/0148872 A1* | 5/2014 | Goldwasser | A61N 1/36082 607/45 |
| 2014/0160250 A1* | 6/2014 | Pomerantz | H04N 5/23229 348/47 |
| 2014/0160424 A1* | 6/2014 | Benko | G06F 1/163 351/158 |
| 2014/0171820 A1* | 6/2014 | Causevic | A61B 5/04845 600/544 |
| 2014/0180158 A1* | 6/2014 | Cheng | A61B 5/6803 600/544 |
| 2014/0206323 A1* | 7/2014 | Scorcioni | H04W 4/16 455/414.1 |
| 2014/0211593 A1* | 7/2014 | Tyler | A61B 5/165 367/137 |
| 2014/0213874 A1* | 7/2014 | Tong | A61B 5/0478 600/383 |
| 2014/0221779 A1* | 8/2014 | Schoonover | A61B 5/4806 600/301 |
| 2014/0223462 A1* | 8/2014 | Aimone | A61B 5/0476 725/10 |
| 2014/0267005 A1* | 9/2014 | Urbach | G06F 3/016 345/156 |
| 2014/0267401 A1* | 9/2014 | Urbach | G06T 11/60 345/633 |
| 2014/0275875 A1* | 9/2014 | Su | A61B 5/684 600/323 |
| 2014/0276183 A1* | 9/2014 | Badower | A61B 5/0476 600/544 |
| 2014/0277582 A1* | 9/2014 | Leuthardt | A61F 2/54 623/25 |
| 2014/0288614 A1* | 9/2014 | Hagedorn | A61B 5/0482 607/45 |
| 2014/0316230 A1* | 10/2014 | Denison | A61B 5/04012 600/383 |
| 2014/0323900 A1* | 10/2014 | Bibian | A61B 5/0476 600/544 |
| 2014/0333529 A1* | 11/2014 | Kim | G06F 3/04842 345/156 |
| 2014/0337036 A1* | 11/2014 | Haiut | G06F 1/3265 704/275 |
| 2014/0375545 A1* | 12/2014 | Ackerman | G06F 3/017 345/156 |
| 2015/0005841 A1* | 1/2015 | Pal | A61N 1/0476 607/45 |
| 2015/0018705 A1* | 1/2015 | Barlow | A61B 5/0484 600/544 |
| 2015/0079560 A1 | 3/2015 | Cowan | |
| 2015/0297109 A1* | 10/2015 | Garten | A61B 5/04845 600/544 |
| 2016/0239937 A1* | 8/2016 | Kim | G06T 1/20 |
| 2016/0241947 A1* | 8/2016 | Degraye | H04R 3/12 |
| 2016/0330182 A1* | 11/2016 | Jeon | H04L 63/062 |
| 2016/0353195 A1* | 12/2016 | Lott | H04R 1/1041 |
| 2017/0071525 A1* | 3/2017 | Lin | A61B 5/18 |
| 2017/0100032 A1* | 4/2017 | Zakariaie | A61B 3/113 |
| 2017/0142507 A1* | 5/2017 | Chang | H04R 1/02 |
| 2017/0173296 A1* | 6/2017 | Park | A61B 5/024 |
| 2017/0195794 A1* | 7/2017 | Vaynberg | H04R 5/033 |

FOREIGN PATENT DOCUMENTS

| | | |
|---|---|---|
| WO | 2016083807 A1 | 6/2016 |
| WO | 2016119664 A1 | 8/2016 |

OTHER PUBLICATIONS

International Search Report and Written Opinion for International Application No. PCT/US2018/034401, dated Sep. 3, 2018, 12 pp.

(56) References Cited

OTHER PUBLICATIONS

International Search Report and Written Opinion for International Application No. PCT/US2018/014887, dated Mar. 21, 2018, 12 pp.

* cited by examiner

ACTIVE UNIPOLAR DRY ELECTRODE OPEN EAR WIRELESS HEADSET AND BRAIN COMPUTER INTERFACE

BACKGROUND

Aspects of the present disclosure relate to wireless technology and, more particularly, to hands-free control of wireless technology.

Wearable devices are electronic devices that are configured to be worn on a user's body and perform various functions, including collecting biometric data for health monitoring. According to an example, electrodes on a wearable device are used to measure electrophysiological signals. These electrophysiological signals can be used to identify patterns in, for example, a user's brain wave activity and identify abnormalities. The abnormalities may be used for diagnostic purposes, as they may be indicative of neurological disorders.

As the types of wearable technology increases and in-view of the projected advancements of wireless communications, including the Internet of Things, it may be beneficial to use collected electrical signals for other purposes.

SUMMARY

All examples and features motioned herein can be combined in any technically possible manner.

According to one example, an open-ear wireless headset including a transducer is used to obtain biologically-relevant information associated with a user. As described in more detail herein, the open-ear wireless headset may take different forms. Regardless of the form taken, the open-ear wireless headset comprises one or more electrodes used to collect biologically-relevant information associated with a user of the open-ear wireless headset.

According to an aspect, a wearable audio product for obtaining biologically-relevant information associated with a user is provided. The audio product comprises a first electrode placed over the user's auditory cortex on a first side of the user's body, a second electrode placed on the first side of the user's body, a first reference electrode placed on the first side of the user's body, a processor coupled to the first, second, and first reference electrode, the processor configured to take one or more actions based on signals received from the first, second, and first reference electrodes, and an electroacoustic transducer coupled to the processor.

According to aspects, the second electrode is placed over one of: the user's occipital lobe, the bridge of the user's nose, or in an ear canal of the user. According to an example, the first reference electrode is placed on the skull of the user behind the user's ear.

According to an example, the audio product performs noise-cancelling between signals received from the first reference electrode and signals received from the first and second electrodes.

According to aspects, the audio product further comprises a third electrode placed over the user's auditory cortex on a second side of the user's body, a fourth electrode placed on the second side of the user's body, and a second reference electrode placed on the second side of the user's body and the processor is further configured to take one or more actions based on signals received from the third, fourth, and second reference electrodes.

According to an example, the audio product applies a first closed feedback loop for signals received from the first side of the body, applies a second closed feedback loop for signals received from the second side of the body, and removes noise from the received signals based on the first and second closed feedback loops.

According to aspect, the audio product determines a state of the user based on the signals received via at least one of the first electrode, the second electrode, or the first reference electrodes and the audio product takes one or more actions based on the determined state.

According to an example, the audio product determines a drop in impedance of signals received via at least one of the first electrode, the second electrode, or the first reference electrode and in response to the determined drop in impedance, the audio product determines the user is stressed. As described in more detail herein, the product determines with an increased confidence that the user is stressed. For example, the drop in impedance increases the confidence or likelihood that the user is stressed.

According to an aspect, the audio product tracks a type of music played in response to determining the user is stressed. In response to determining the user is stressed, the audio product recommends at least one of a song or melody based on the tracked type of music.

According to an example, the audio product of determines a decreased rate of blinking of the user based on signals received via at least one of the first and second electrodes. In response to the determined decreased rate of blinking, the product determines the user is focused. As described in more detail herein, the product determines with an increased confidence that the user is trying to focus. For example, the determined decreased rate of blinking increases the confidence or likelihood that the user is trying to focus.

According to an aspect, the audio product determines (with an increased confidence) the user is focused and, in response, recommends a certain song or melody.

According to an example, the audio product determines the state of the user by measuring jaw movements based on signals received from at least one of the first electrode, the second electrode, or the first reference electrode. In response to the measured jaw movements, the audio product determines the user is talking. According to an example, signals received from the auditory cortex in combination determined jaw movements are used to determine, with increased confidence or increased likelihood, the user is talking.

According to an aspect, the audio product adjusts a volume of music played in response to determining the user is talking.

According to an example, the audio product triggers automatic speech recognition (ASR) in response to determining the user is talking. According to an example, the audio product enters a low power mode in response to determining the user is not talking.

According to an aspect, a method for obtaining biologically-relevant information associated with a user from wearable audio product including an electroacoustic transducer is provided. The method generally includes receiving electrical signals via a first electrode placed over the user's auditory cortex on a first side of the user's body, receiving electrical signals via a second electrode placed on the first side of the user's body, receiving electrical signals via a first reference electrode placed on the first side of the user's body, and taking one or more actions based, at least in part, on the signals received from the first, second, and reference electrodes.

According to an example, the second electrode is placed over one of the user's occipital lobe, the bridge of the user's nose, or in an ear canal of the user.

According to an aspect, a wearable audio product including an electroacoustic transducer for obtaining biologically-relevant information associated with a user is provided. The wearable audio product comprises a first electrode, a second electrode, and a first reference electrode each placed on a first side of the user's body. The audio product comprises a third electrode, a fourth electrode, and a second reference electrode each placed on a second side of the user's body. The audio product comprises a processor coupled to the first, second, third, fourth, first reference, and second reference electrodes, wherein the processor is configured perform noise canceling on signals received via the first, second, third, and fourth electrodes and control the device based on the noise-canceled signals.

According to an example, the first and third electrodes are placed over the first and second side of the auditory cortex of the user, respectively. According to an example, the second and fourth electrodes are placed over one of: the first and second side of the user's occipital lobe, the first and second side of a bridge of the user's nose, or in each ear canal of the user.

DETAILED DESCRIPTION

Aspects of the present disclosure relate to a single integrated wearable product configured to collect biologically-relevant information associated with a user of the wearable product. The wearable product may take one or more actions to intelligently control itself based on the collected information. The collected information is used to determine a state of the user. As described below, a state of a user is not absolute. Accordingly, the collected information is used to determine, for example, with an increased confidence level or an increased likelihood, a particular state of a user. Example states of a user include stressed, not stressed, focused, not focused, talking, eating, or minimal jaw movement. The determined state of the user is used to trigger actions of the wearable device, such as changing a type of music played, changing the volume of the music, acknowledging a notification, or triggering automatic speech recognition (ASR). According to one example, the wearable product is an audio product. The audio product may take one of several form factors. Example form factors are provided in FIGS. 1A, 1B, and 1C.

Figure 1:
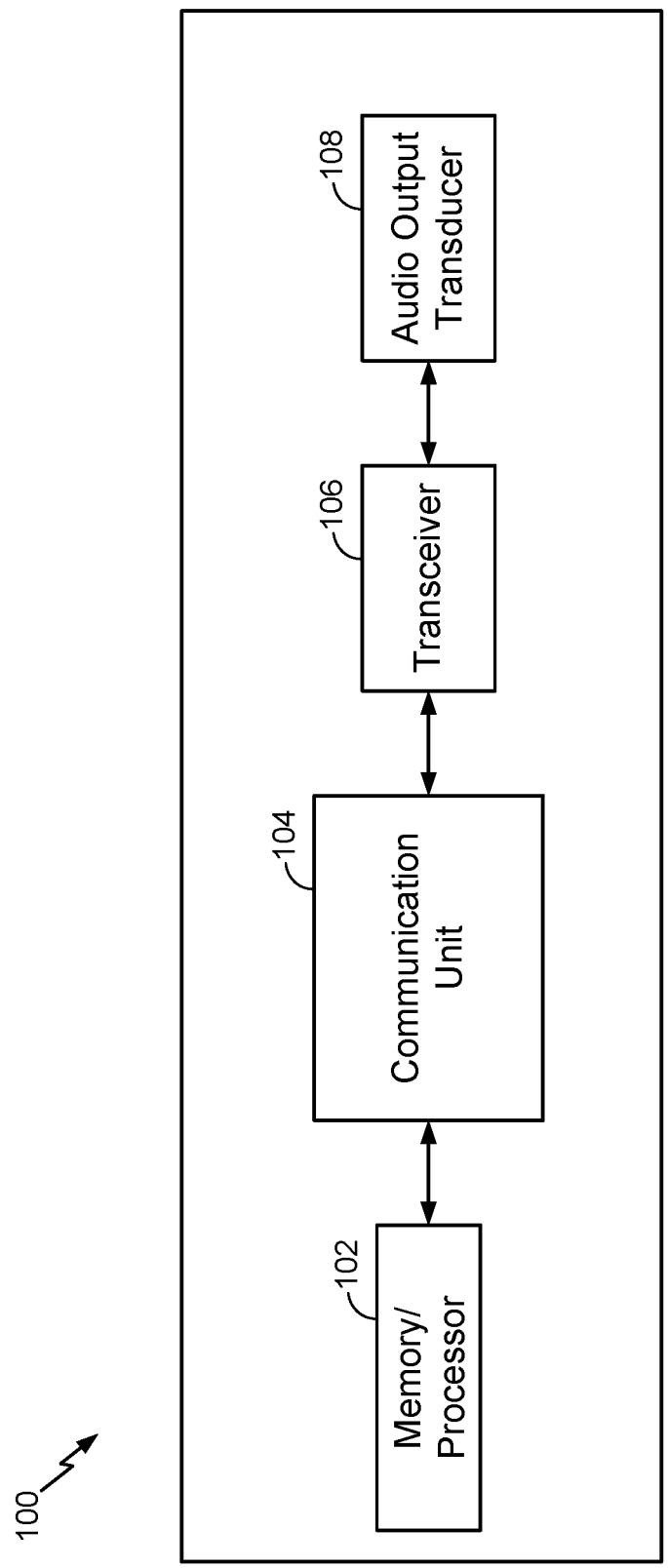
FIG. 1 is a block diagram of a wireless device.

FIG. 1 illustrates example components of a wireless device 100, for example an integrated wearable product such as an audio product. According to one example, the audio product is an open-ear wireless headset including a transducer 108. The wireless device includes a memory and processor 102, communication unit 104, transceiver 106, and audio output transducer 108. The memory may include Read Only Memory (ROM), a Random Access Memory (RAM), and/or a flash ROM. The memory stores program code for controlling the memory and processor 102. The memory and processor 102 control the operations of the wireless device 100. Any or all of the components in FIG. 1 may be combined into multi-function components.

The processor 102 controls the general operation of the wireless device 100. For example, the processor 102 performs process and control for audio and/or data communication. In addition to the general operation, the processor 102 initiates processing signals received from electrodes of the wireless device 100 to control the wireless device 100 as described in more detail herein.

The communication unit 104 facilitates a wireless connection with one or more other wireless devices. For example, the communication unit 104 may include one or more wireless protocol engines such as a Bluetooth engine. While Bluetooth is used as an example protocol, other communication protocols may also be used. Some examples include Bluetooth Low Energy (BLE), Near Field Communications (NFC), IEEE 802.11, or other local area network (LAN) or personal area network (PAN) protocols.

The transceiver 106 transmits and receives information via one or more antennae to exchange information with one or more other wireless devices. According to aspects, the transceiver 106 includes one or more microphones. The transceiver 106 is not necessarily a distinct component. The transceiver 106 may be implemented entirely in software executed by the communication unit 104.

The audio output transducer 108 may be also known as a driver or speaker. In some examples, more than one output transducer is used. The transducer converts electrical signals into sound and converts sound into electrical signals.

The wireless device 100 includes multiple electrodes, configured to receive electrical signals from a user of the wireless device. The electrodes may be active, unipolar, dry electrodes. According to one example, the wireless device has two data-collecting electrodes and one reference electrode. The first and second data-collecting electrodes and the first reference electrode each contact a first side of the user's body. For example, each of these three electrodes contacts either a left side or right side of the user's body. Any of the data-collecting electrodes and reference electrodes can include a cluster of electrodes positioned in the specific areas described herein. The cluster of electrodes in the specific location may be viewed as an electrode.

Figure 1A:
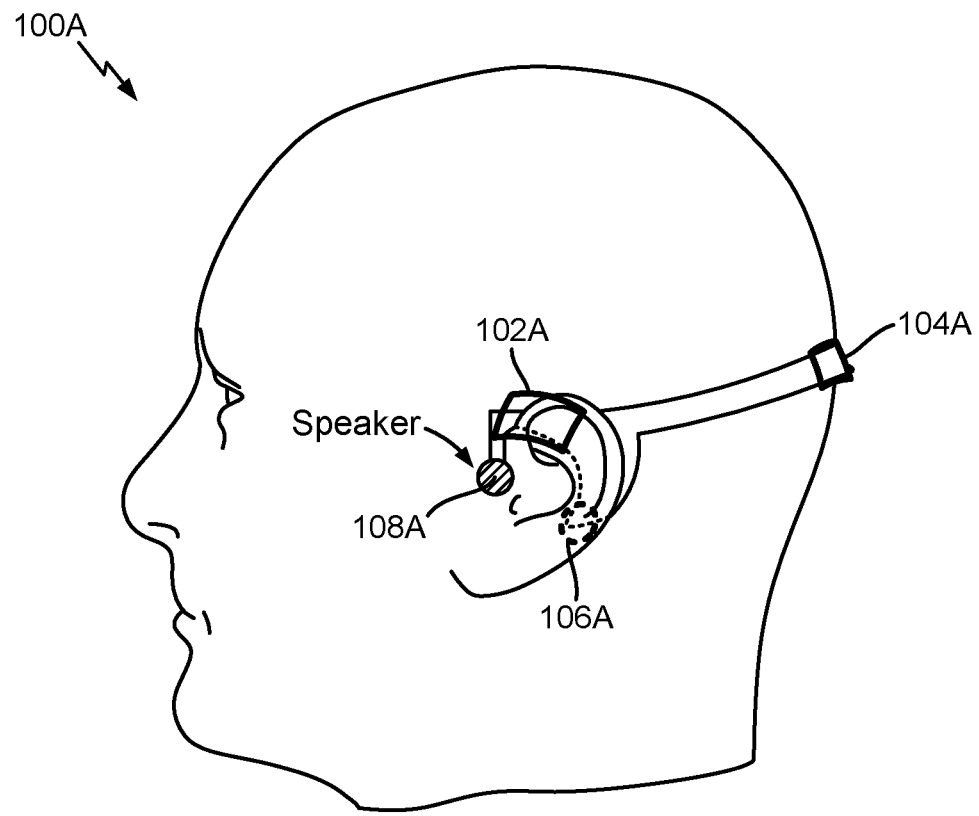
FIGS. 1A-1C illustrate example form factors for the wireless device.
Figure 1A:
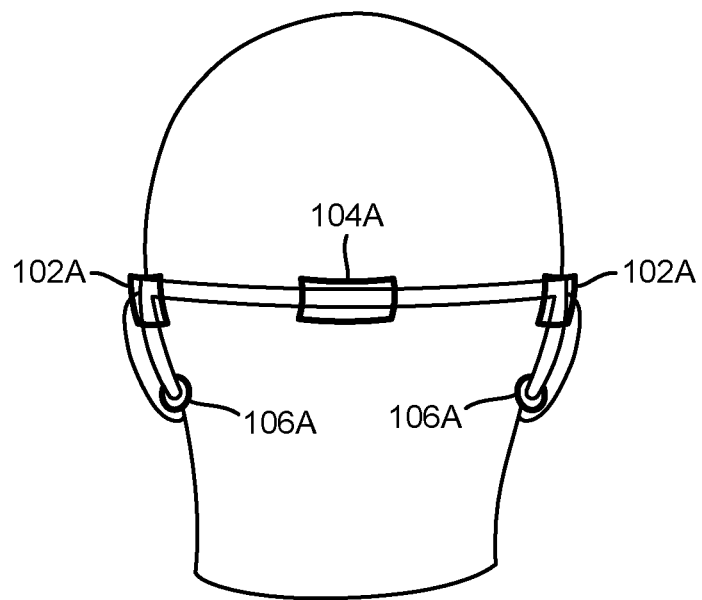
Figure 1B:
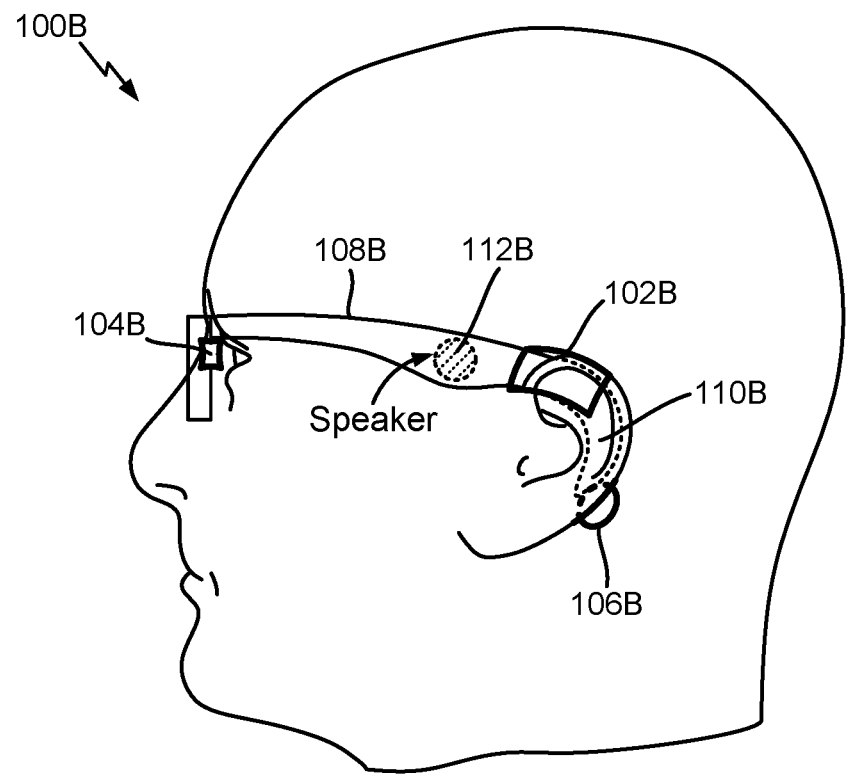
Figure 1B:
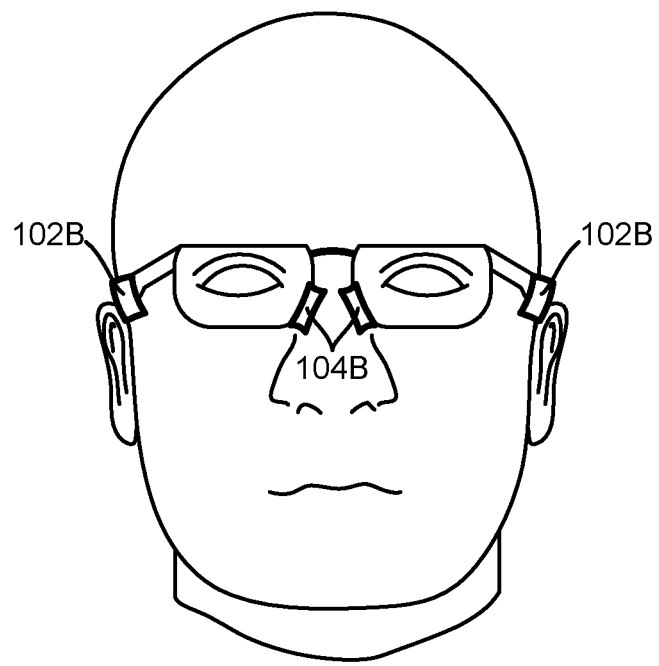
Figure 1C:
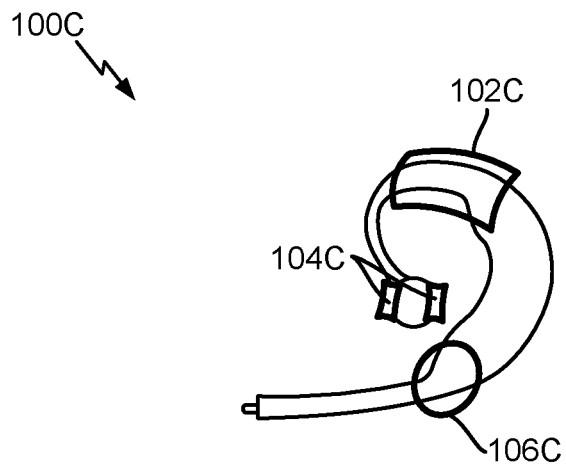
Figure 1C:
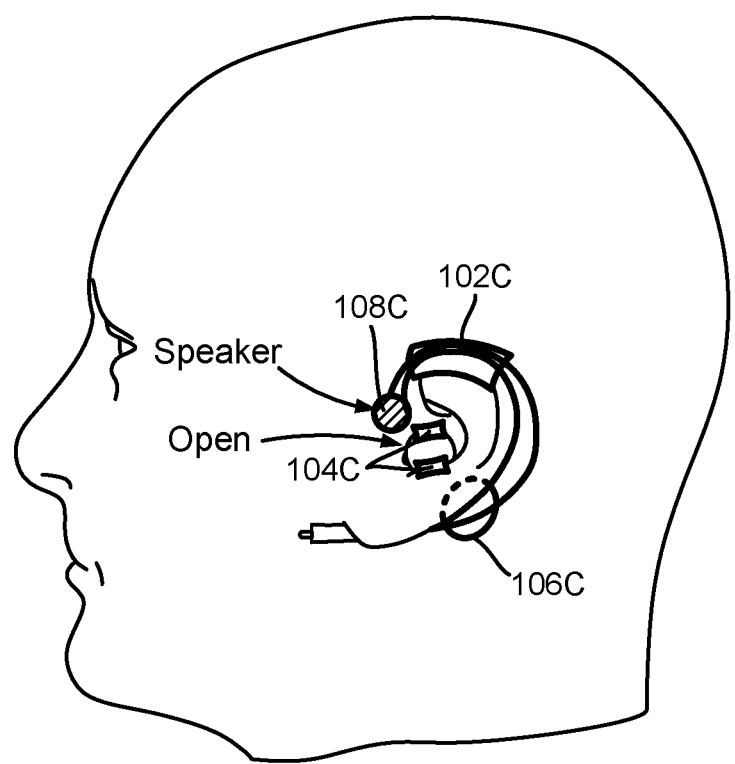

The first electrode is placed over the user's auditory cortex on the same side of the user's body as the second electrode and the first reference electrode. The second electrode is placed over one of the user's occipital lobe (for example, as illustrated in FIG. 1A), the bridge of the user's nose (for example, as illustrated in FIG. 1B), or contacts an ear canal of the user (for example, as illustrated in FIG. 1C). According to an example, the first reference electrode is placed on the skull of the user, behind the user's ear.

FIG. 1A illustrates an example form factor 100A wherein the open-ear wireless headset includes a band covering part of the user's occipital lobe. The band stretches from above and behind the user's right ear, behind the back of the head covering the occipital lobe, to above and behind the user's left hear. The form factor 100A includes at least one speaker 108A. According to an example, a speaker 108A hangs over or is proximate to at least a portion of the user's ear.

According to an example, the first electrode 102A is placed on the band, over the user's ear on one side of the user's body to monitor the auditory cortex. The second electrode 104A is placed on the band, behind the back of the head on the same side of the user's body as the first electrode. As illustrated, the second electrode 104A is placed over the user's occipital lobe. The first reference electrode 106A is placed on any other portion of the form factor 100A.

The pressure exerted by the band on the user's head enables the first and second data-collecting electrodes 102A, 104A and the first reference electrode 106A to contact the user's head and measure electrical signals from the occipital lobe, auditory cortex, and reference location.

FIG. 1B illustrates an example form factor 100B wherein the second electrode is placed on the bridge of the user's nose. According to the illustrated example, form factor 100B comprises glasses. Each temple 108B and temple tip 110B of the glasses 100B rest over an ear of the user. According to an example, a speaker 112B is placed inside a temple 108B. For example, the temple 108B has an opening towards the user's body. The speaker 112B is located in this opening.

The first electrode 102B configured to monitor the auditory cortex is placed on the temple 108B or temple tip 110B. The second electrode 104B is placed on the bridge or nose pad of the glasses. The first reference electrode 106B is placed on any other portion of the glasses 110B or on a band (such as one similar to 100A), which connects each of the temple tips 110B and covers the user's occipital lobe.

FIG. 1C illustrates an example form factor 100C wherein the second electrode is placed in an ear canal of the user. According to the illustrated example, form factor 100C comprises an headset. The headset is a C-shaped headset, wherein a "C" shaped clip hooks behind a user's ear. The headset may be an open ear headset. The ear tip is inserted inside the user's ear. According to an aspect, the ear tip is made of a flexible material, which conforms to the shape of the user's ear and creates a gentle seal with the ear canal. Similar to form factor 100A illustrated in FIG. 1A, speaker 108C hangs over or is proximate to at least a portion of the user's ear.

The first data-collecting electrode 102C is place on the "C" shaped portion behind the user's ear to monitor signals from the auditory cortex. According to aspects, the first data-collecting electrode 102C monitors signals such as an electrooculogram (EOG), electrocardiogram (EKG), electromyogram (EMG), or electroencephalogram (EEG). The second data-collecting electrode 104C is placed on the ear tip. The second data-collecting electrode 104C monitors signals such as EOG, EKG, EMG, or EEG. The first reference electrode 106C is placed on any other portion of the headset 100C or on a band (such as one similar to 100A), which connects each of the left and right ear pieces of the headset and covers the occipital lobe. According to an example, the first reference electrode 106C is wirelessly connected to the first and second data-collecting electrodes 102C and 104C. Accordingly, the band does not necessarily physically connect the left and right ear pieces of the headset.

According to an example, the wireless device implemented using any form factor also has third and fourth data-collecting electrodes and a second reference electrode. The third and fourth data-collecting electrodes and the second reference electrode each contact a same side of the user's body. Assuming the first and second data-collecting electrodes and the first reference electrode each contact a left side of the user's body, the third and fourth data-collecting electrodes and the second reference electrode each contact a right side of the user's body.

The third electrode is placed over the user's auditory cortex on the same side of the user's body as the fourth electrode and the second reference electrode. The fourth electrode is placed over one of the user's occipital lobe, the bridge of the user's nose, or in an ear canal of the user.

As described above, when the fourth electrode is placed over the user's occipital lobe, the wireless device may comprise a band that stretches from above and behind the user's ear on a first side of the body, behind the back of the head covering the occipital lobe of the user, to above and behind the user's ear on a second side of the body. Assuming the first and second data-collecting electrodes and the first reference electrode each contact a left side of the user's body, the third electrode may be placed above the user's right ear to monitor the auditory cortex. The fourth electrode may be placed behind the back of the head on the right side of the user's body to monitor the occipital lobe. The second reference electrode is placed on any other portion of the band. As described above, the pressure exerted by the band on the user's head enables the electrodes to contact the user's head and measure electrical signals from the auditory cortex, occipital lobe, and reference location.

Similarly, when the fourth electrode is placed on the bridge of the user's nose, the wireless device may comprise glasses. Assuming the first and second data-collecting electrodes and the first reference electrode each contact a left side of the user's body, the third and fourth data-collecting electrodes and second reference electrode are placed on the right side of the user's body. Accordingly, the third electrode is placed on the right temple or right temple tip of the glasses. The fourth electrode is placed on the right side of the bridge or on the right nose pad of the glasses. The second reference electrode is placed on any other portion of the glasses contacting the right side of the user's body or on a right side of the band, which connects each of the temple tips and covers the occipital lobe of the user.

When the fourth electrode is place in an ear canal of the user, the wireless device may comprise a headset. According to an example, the headset is a C-shaped headset, such as an open-ear headset. Assuming the first and second data-collecting electrodes and the first reference electrode each contact a left side of the user's body, the third and fourth data-collecting electrodes and the second reference electrode are placed on a portion of the headset contacting the rights side of the user's body. According to an example, the third data-collecting electrode is placed on the "C" shaped portion behind the user right ear, the fourth data-collecting electrode is placed on the right ear, and the second reference electrode is placed on any other portion of the headset or on a band contacting the right side of the user, wherein the band connects each of the left and right ear pieces of the headset and covers the user's occipital lobe.

Each of the first to fourth data-collecting electrodes and first and second reference electrodes includes one or multiple electrodes. According to an example two, three, or any integer number of electrodes may be clustered in the areas specified above (102A-106A, 102B-106B, and 102C-106C). The cluster of electrodes in one location may be collectively referred to as an electrode.

Figure 2:
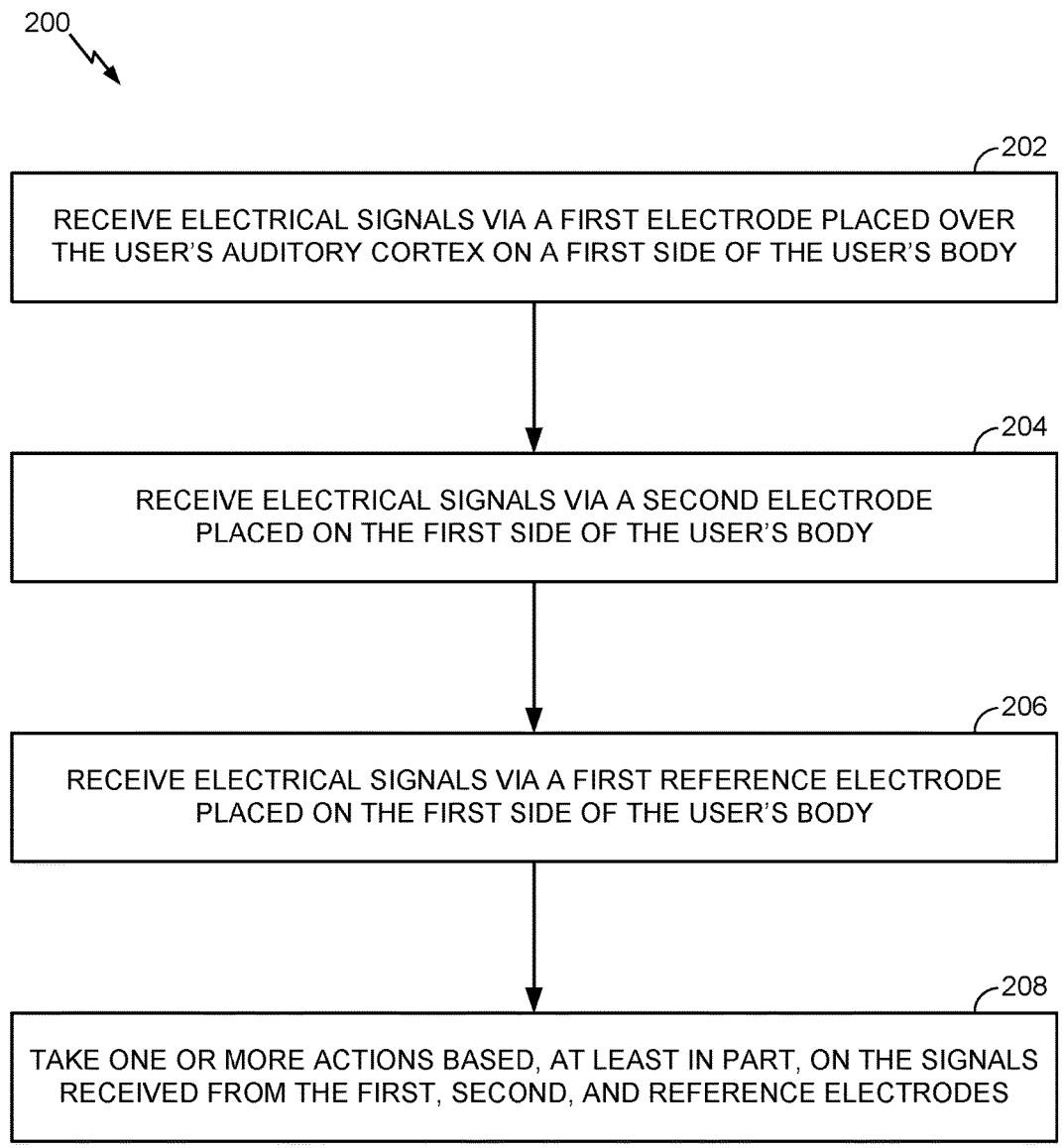
FIG. 2 is a flow diagram illustrating example steps performed by a wearable audio product for obtaining biologically-relevant information associated with a user of the product.

FIG. 2 illustrates example operations 200 performed by a wearable audio product. The wearable audio product has one or more of the components illustrated in FIG. 1.

At 202, the audio product receives electrical signals via a first electrode placed over the user's auditory cortex on a first side of the user's body. At 204, the audio product receives electrical signals via a second electrode placed on the first side of the user's body. The second electrode is placed over one of the user's occipital lobe, the bridge of the user's nose, or in an ear canal of the user.

At 206, the audio product receives electrical signals via a first reference electrode placed on the first side of the user's body. According to an example, the reference electrode is placed at any location on the audio product that is different than the location of the first and second electrodes.

At 208, the audio product takes one or more actions based, at least in part, on the signals received from the first, second, and reference electrodes. According to an example, the audio product also receives electrical signals via a third electrode placed over the user's auditory cortex on a second side of the user's body, a fourth electrode placed on the second side of the user's body, and a second reference electrode placed on the second side of the user's body, wherein the all of the described electrodes are part of the audio product. In an effort to remove noise from the collected signals, the audio product performs noise-cancelling on signals received from the four data-collecting electrodes.

Figure 3:
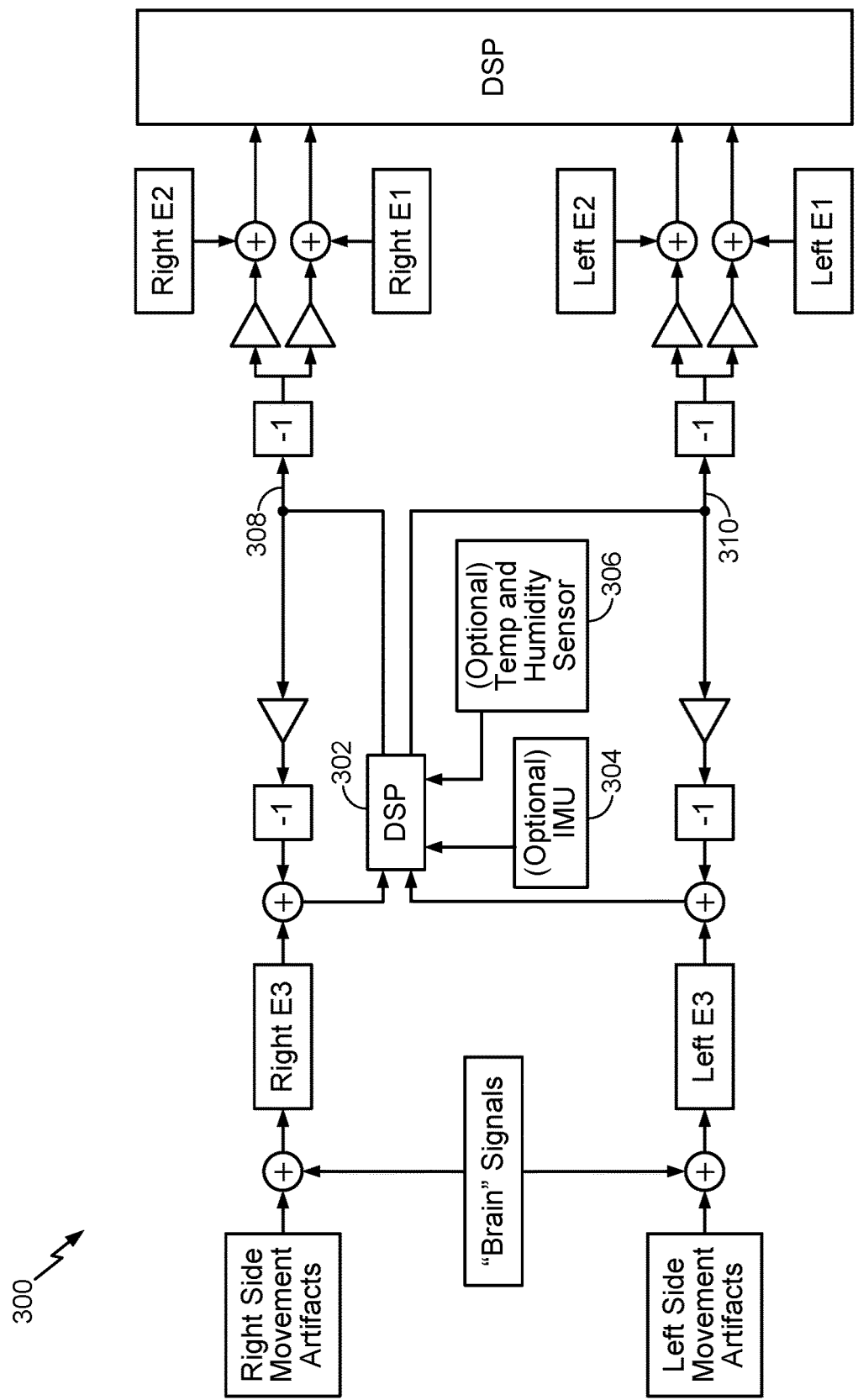
FIG. 3 illustrates an example of processing signals received from the first to fourth data-collecting electrodes.

FIG. 3 illustrates an example 300 of signal processing performed by the wearable audio product. Left E1 and Left E2 refer to the first and second data-collecting electrodes and Right E1 and Right E2 refer to the third and fourth data-collecting electrodes. Left E3 refers to the first reference electrode and Right E3 refers to the right reference electrode.

The digital signal processor (DSP) 302 processes a combined signal from the left side movement artifacts, the brain, and Left E3. DSP 302 also processes a combined signal from the right side movement artifacts, brain signals, and Right E3. The DSP 302 performs short-time Fourier transform and compares the combined signal from the left and right side and outputs a difference per side at 308 and 310. In an effort to remove noise, the DSP 302 optionally receives an output from an inertial measurement unit (IMU) 304 and/or from a temperature and humidity sensor 306. The IMU 304 accounts for entire body movements such as running or walking. The temperature and humidity sensor 306 may be used by the DSP to adjust a gain based on the ambient temperate and humidity.

The wearable audio product applies one closed feedback loop for signals collected from each side of the user's body in an effort to remove noise from the collected signals. The feedback loop associated with the left side of the user's body is between Left E3 against Left E1 and Left E2. The feedback loop associated with the right side of the user's body is between Right E3 against Right E1 and Right E2.

Signals received from each side of the body are cross-correlated and noise may be further reduced by comparing the difference signal against an audio stream, in an effort to remove noise that is induced or coupled from the speakers or wires in the audio product.

Using signals received from at least one side of the body (for example, Left E1, Left E2, and Left E3) and/or using noise-reduced signals from at least one side of the body, the audio product determines, with increased confidence, a state of the user. Example states of the user include determining the user is stressed (or not stressed), focused (or not focused), or moving a jaw (or not moving/having minimal jaw movement). As states of a user are not absolute, the signals received via the electrodes are used to determine an increased likelihood the user is in a particular state. Furthermore, according to an example, other biolsignals such as the user's heart rate, respiration rate, movement from IMU, etc. are used in conjunction with the signals collected using the above-described electrodes to determine an increased likelihood the user is in a particular state.

The audio product determines a user is stressed (or not stressed) by measuring overload in the user's auditory cortex (from the first or third data-collecting electrode). The user's autonomous nervous system may cause sweat glands to secrete sweat. The conductive sweat may cause a drop in impedance measured by data-collected electrodes, the reference electrodes, or a combination thereof.

The audio product determines a user is focused (or not focused) by measuring occipital cortex overload in, for example, the alpha band (8-13 Hz). Occipital cortex overload may be measured using the electrode placed over the occipital band (for example, the second or fourth data collecting electrode). An overload of measured activity in the occipital cortex indicates the user is focused.

The audio product determines a user is focused (or not focused) by measuring a rate of blinking. Blinking rates are measured from EMG or EOG signals. EMG or EOG signals may be measured using at least one of the first to fourth data-collecting electrodes. The processor may compare signals from both the left and right sides of the user to differentiate between a blink versus a wink or eye twitch. The audio product may collect data over time to determine the user's average blink rate. According to aspects, the audio product uses a moving average filter for signals obtained via the occipital cortex for determining eye movement. A decreased rate of blinking or eye movement indicates the user is focused.

The audio product determines a user is moving a jaw by measuring EMG signals using any of the above-described electrodes. According to an example, jaw movements indicate the use is talking or chewing. According to an example, signals received from the auditory cortex in combination determined jaw movements are used to determine, with increased confidence, the user is talking.

The state of the user determined by the audio product is used to intelligently control the audio product itself. According to one example, the audio product enters a low-power state when the user is not talking. The ASR engine listens using microphones of the product when the user is talking. According to an example, the ASR engine listens for the Wake Up Work (WUW), which triggers ASR. This increases a user's privacy because the audio product is not always listening to the user and reduces battery consumption due to decreased high frequency sampling. Over time, a neural network may be trained to learn the user's EMG pattern correlated with a WUW thereby reducing false voice personal assistant (VPA) triggers.

According to an example, the audio product dynamically adjusts the volume of music played when it determines the user is talking. Accordingly, the user does not have to manually decrease or mute the music. When the audio product determines the user is no longer speaking, it increases the volume. In this manner, the audio product enables seamless, intelligent, hands-free operations of the audio product.

According to an example, the audio product correlates certain eye movements with actions such as changing the volume, changing songs, or acknowledging notifications. Accordingly, EMG readings from blinking, which are discernable based on signals received from signals received via the auditory electrodes, enable hands-free operation of the audio product.

According to another example, the electrodes may discern when a tip of the tongue, having an overall negative charge, touches the inside of the user's cheek. The audio product may correlate certain tongue-to-cheek patterns with actions such as changing the volume, changing songs, or acknowledging notifications.

After determining the user is stressed (or not stressed), the audio product may track what songs the user listens to while stressed (or not stressed). The audio product may also track the songs the user listens to while focused (or not focused).

According to an example, the audio product learns what songs or melodies the user listens to when transitioning from a stressed state to a not stressed state. According to an aspect, the audio product transmits a determined state of the user to an external cloud. Based on the songs a user listens to while focused (or not focused), the cloud learns which songs or melodies the user listens to when transitioning form a stressed state to a not stressed state. The cloud communicates song and/or melody recommendations to the audio product. Accordingly, the audio product may accurately recommend or play songs base on the user's determined state.

The audio product may enhance personalization by training neural networks to learn the phrasing and melodies associated with the user's frequently-played songs. In response to determining the user is stressed or focused, the audio product may play one or more songs having similar phrasing or melodies.

As described herein, multiple electrodes on an audio product are used to collect biologically-relevant information associated with a user. The collected information is used to ascertain a state of the user. Based on the determined state of the user, the audio product takes one or more actions to intelligently adapt or respond to the user. In this manner, the audio product provides personalized, hands-free control.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

The invention claimed is:

1. A wearable audio product for obtaining biologically-relevant information associated with a user comprising:
   a first electrode placed over the user's auditory cortex on a first side of the user's body;
   a second electrode placed on the first side of the user's body;
   a first reference electrode placed on the first side of the user's body;
   a third electrode placed over the user's auditory cortex on a second side of the user's body;
   a fourth electrode placed on the second side of the user's body; and
   a second reference electrode placed on the second side of the user's body,
   a processor coupled to the first, second, first reference, third, fourth, and second reference electrodes, the processor configured to take one or more actions based on signals received from the first, second, first reference, third, fourth, and second reference electrodes,
   wherein taking the one or more actions comprises:
   combining signals from first side movement artifacts, the user's brain signals detected by the first and second electrodes, and the first reference electrode to generate a combined first side signal;
   combining signals from second side movement artifacts, the user's brain signals detected by the third and fourth electrodes, and the second reference electrode to generate a combined second side signal;
   comparing the combined first side signal and the combined second side signal to output a difference for the first side and a difference for the second side;
   applying a first closed feedback loop for signals received from the first side of the body including the difference for the first side signal,
   applying a second closed feedback loop for signals received from the second side of the body including the difference for the second side signal, and
   removing noise from the received signals based on the first and second closed feedback loops, wherein removing the noise comprises cross-correlating the signals received from the first side of the body with the signals received from the second side of the body; and
   an electroacoustic transducer coupled to the processor.

2. The audio product of claim 1, wherein one of the second electrode or the fourth electrode is placed over one of: the user's occipital lobe or in an ear canal of the user.

3. The audio product of claim 1, wherein one of the first reference electrode or the second reference electrode is placed on the skull of the user behind the user's ear.

4. The audio product of claim 1, wherein taking the one or more actions further comprises:
   determining a state of the user based on the signals received via the first side of the body comprising the first electrode, the second electrode, and the first reference electrode, or the second side of the body comprising the third electrode, the fourth electrode, and the second reference electrode; and
   taking the one or more actions based on the determined state.

5. The audio product of claim 4, wherein determining the state of the user further comprises:
   determining a drop in impedance of the signals received via at least one of the first electrode, the second electrode, the first reference electrode, the third electrode, the fourth electrode, and the second reference electrode; and
   in response to the determined drop in the impedance, determining the state of the user is stressed.

6. The audio product of claim 5, wherein taking the one or more actions based on the determined state comprises:
   tracking a type of music played by the audio product in response to determining the state of the user is stressed; and in response to determining the state of the user is stressed, recommending at least one of a song or melody based on the tracked type of music.

7. The audio product of claim 4, wherein determining the state of the user further comprises:
   determining a decreased rate of blinking of the user based on the signals received via at least one of the first electrode, the second electrode, the third electrode, and the fourth electrode; and in response to the determined decreased rate of blinking, determining the user is focused.

8. The audio product of claim 7, wherein taking the one or more actions based on the determined state comprises:
   in response to determining the user is focused, recommending a certain song or melody played by the audio product.

9. The audio product of claim 4, wherein determining the state of the user further comprises:
   measuring jaw movements based on the signals received from at least one of the first electrode, the second electrode, the first reference electrode, the third electrode, the fourth electrode, and the second reference electrode; and
   in response to the measured jaw movements, determining the user is talking.

10. The audio product of claim 9, wherein taking the one or more actions based on the determined state comprises:
adjusting a volume of music played by the audio product in response to determining the user is talking.

11. The audio product of claim 9, wherein taking the one or more actions based on the determined state comprises:
triggering automatic speech recognition (ASR) in response to determining the user is talking.

12. The audio product of claim 9, wherein taking the one or more actions based on the determined state comprises:
entering a low power mode in response to determining the user is not talking.

13. A method for obtaining biologically-relevant information associated with a user from a wearable audio product including an electroacoustic transducer coupled to a processor, comprising:
receiving, by the processor, electrical signals via a first electrode placed over the user's auditory cortex on a first side of the user's body;
receiving, by the processor, electrical signals via a second electrode placed on the first side of the user's body;
receiving, by the processor, electrical signals via a first reference electrode placed on the first side of the user's body;
receiving, by the processor, electrical signals via a third electrode placed over the user's auditory cortex on a second side of the user's body;
receiving, by the processor, electrical signals via a fourth electrode placed on the second side of the user's body;
receiving, by the processor, electrical signals via a second reference electrode placed on the second side of the user's body; and
taking, by the processor, one or more actions based, at least in part, on the signals received from the first, second, first reference, third, fourth, and second reference electrodes, wherein taking the one or more actions comprises:
combining the signals from first side movement artifacts, the user's brain signals detected by the first and second electrodes, and the first reference electrode to generate a combined first side signal;
combining the signals from second side movement artifacts, the user's brain signals detected by the third and fourth electrodes, and the second reference electrode to generate a combined second side signal;
comparing the combined first side signal and the combined second side signal to output a difference for the first side and a difference for the second side;
applying a first closed feedback loop for the signals received from the first side of the body including the difference for the first side signal,
applying a second closed feedback loop for the signals received from the second side of the body including the difference for the second side signal, and
removing noise from the received signals based on the first and second closed feedback loops, wherein removing the noise comprises cross-correlating the signals received from the first side of the body with the signals received from the second side of the body.

14. The method of claim 13, wherein the second electrode or the fourth electrode is placed over one of the user's occipital lobe or in an ear canal of the user.

15. A wearable audio product including an electroacoustic transducer for obtaining biologically-relevant information associated with a user comprising:
a first electrode, a second electrode, and a first reference electrode each placed on a first side of the user's body;
a third electrode, a fourth electrode, and a second reference electrode each placed on a second side of the user's body; and
a processor coupled to the first, second, third, fourth, first reference, and second reference electrodes, wherein the processor is configured to:
perform noise canceling on signals received via the first, second, third, and fourth electrodes, wherein performing the noise canceling comprises:
combining signals from first side movement artifacts, the user's brain signals detected by the first and second electrodes, and the first reference electrode to generate a combined first side signal;
combining signals from second side movement artifacts, the user's brain signals detected by the third and fourth electrodes, and the second reference electrode to generate a combined second side signal;
comparing the combined first side signal and the combined second side signal to output a difference for the first side and a difference for the second side;
apply a first closed feedback loop for signals received from the first side of the body including the difference for the first side signal;
apply a second closed feedback loop for signals received from the second side of the body including the difference for the second side signal; and
remove noise from the received signals based on the first and second closed feedback loops, wherein removing the noise comprises cross-correlating the signals received from the first side of the body with the signals received from the second side of the body; and
control the audio-product based on the noise-canceled signals.

16. The wearable audio product of claim 15, wherein the second and fourth electrodes are placed over one of: the first and second side of the user's occipital lobe or in each ear canal of the user.

* * * * *